United States Patent [19]

Jagur

[11] 4,405,771
[45] Sep. 20, 1983

[54] ORGANOMETALLIC POLYMERS, THEIR PREPARATION AND COMPOSITIONS CONTAINING THEM

[75] Inventor: Joseph Jagur, Rehovot, Israel

[73] Assignee: Yeda Research & Development Co., Ltd., Rehovot, Israel

[21] Appl. No.: 312,319

[22] Filed: Oct. 16, 1981

[30] Foreign Application Priority Data

Oct. 27, 1980 [IL] Israel ........................................ 61351

[51] Int. Cl.³ ............................................. C08G 12/06
[52] U.S. Cl. ..................................... 528/266; 528/232; 528/233; 528/234; 528/235; 528/237; 528/239; 528/268
[58] Field of Search .................... 260/429 C; 528/232, 528/233, 234, 235, 237, 239, 266, 268–269, 395; 424/78, 82

[56] References Cited

U.S. PATENT DOCUMENTS

| | | | |
|---|---|---|---|
| 3,166,532 | 1/1965 | Sweeny | 528/233 |
| 3,370,041 | 2/1968 | Kornicker et al. | 528/235 |
| 3,503,739 | 3/1970 | DuBosc et al. | 528/266 |
| 3,516,971 | 6/1970 | Webb | 528/266 |
| 3,810,848 | 5/1974 | Chapurlat et al. | 528/232 |
| 4,172,937 | 10/1979 | Suematu et al. | 528/266 |

*Primary Examiner*—Lucille M. Phynes
*Attorney, Agent, or Firm*—Browdy & Neimark

[57] ABSTRACT

There are provided metal containing polymeric coordination compounds which are prepared by a process which comprises reacting metal salts with polydentate ligand molecules obtained by the condensation of aromatic dialdehydes with $\beta$-hydroxy-$\alpha,\gamma$-diamines. The above are electrical semiconductors. Such polymers containing platinum have a biological activity.

7 Claims, No Drawings

ORGANOMETALLIC POLYMERS, THEIR PREPARATION AND COMPOSITIONS CONTAINING THEM

This invention relates to a novel class of metal containing polymers and more particularly to novel polymeric co-ordination compounds acting as electric semiconductors, to processes of their production, and to the use of such compounds.

An object of the present invention is the preparation of organometallic polymers by reacting metal salts with polydentate ligand molecules obtained by condensation of aromatic dialdehydes with $\beta$-hydroxy-$\alpha,\gamma$-diamines. A further object of the invention is to provide a new class of organometallic polymers having biological activity. Additional objects of the invention will become apparent from the following description and claims.

The new class of the polymeric semi-conducting co-ordination compounds provided by the present invention is characterized by the recurring structural unit groupings, conforming to the following general formulae

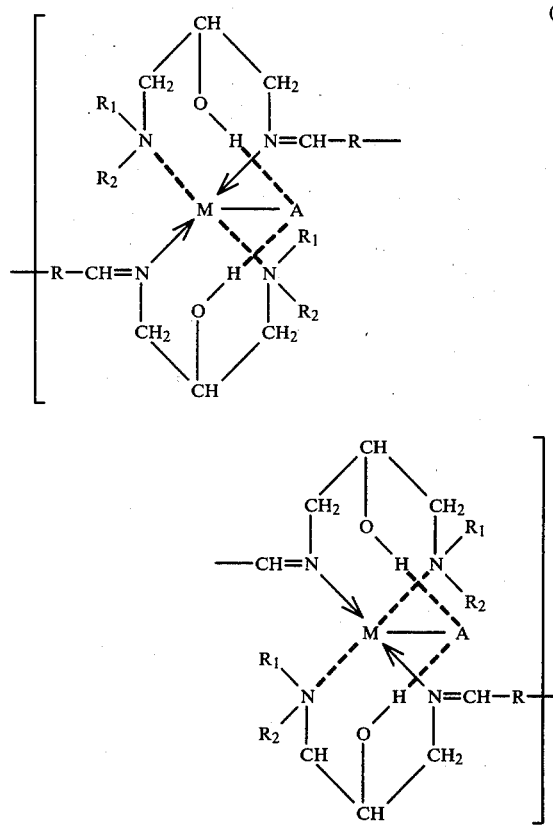

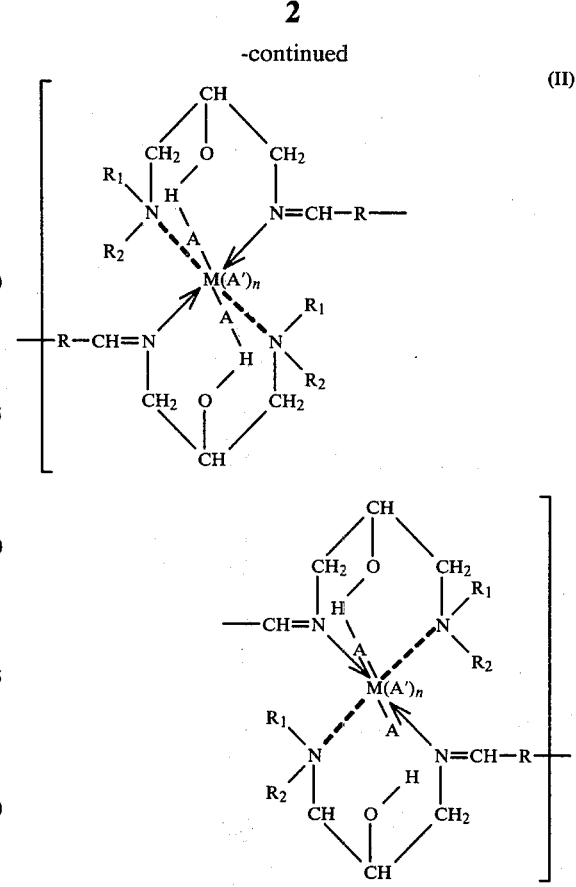

where R is a bivalent aromatic hydrocarbon radical, $R_1$ and $R_2$ are monovalent hydrocarbon radicals and M is a metal cation capable to form co-ordination bonds with imino and amino nitrogens. A or $A^1$ are anions acting as counter ions of the metal cation, M. The number n is equal to zero or is an integer, depending on the valency of the cation M, so as to satisfy the requirement of preservation of the macroscopic electro-neutrality of the system. Various salts of transition metals can be used for the preparation of the polymeric coordination compounds described in the present invention. The suitability of a given salt is primarily determined by the ability of its metal cation, M, to form coordination bonds with the ligand molecules formed by condensation of an aromatic aldehyde with an $\beta$-hydroxy-$\alpha,\gamma$-diamine, and not by the nature of its anions. The compatibility of various anions with the hydrophobic part of the polymeric coordination compounds of the present invention is secured by the incorporation into the ligand molecules of properly spaced hydroxyl groups, which provide hydrogen bonding interactions with the counter ions of the chelated cations. Thus, coordination polymers were prepared with $AgNO_3$, $ZnCl_2$, $CuCl_2$, $Cu(NO_3)_2$, $CoCl_2$, $NiCl_2$, $PeCl_4$, $MnCl_2$, $FeCl_2$, $FeCl_3$, $FeBr_3$, $TiCl_3$, $TiCl_4$, $SbCl_3$ and $Pb(CH_3COO)_2$.

The preparation of the polymeric co-ordination compounds described in the present invention comprises:
a. Condensing an aromatic dialdehyde with an $\beta$-hydroxy-$\alpha,\gamma$-diamine to form the "monomeric" polydentate ligand,
b. preparing a solution of the "monomeric" polydentate ligand in an organic solvent, preferably an aprotic volatile solvent, such as toluene or chloroform, c. dissolving the chosen inorganic salt in the "monomeric" polydentate ligand solution, d. evaporating of the solvent from the thus obtained solution to give a homogeneous coating of the polymeric co-ordination compound on a suitable substrate, or to produce it in the form of flakes or powder, e. if desired baking the thus formed polymeric coordination compound at temperatures ranging from 100°–150° C.

The baking operation is primarily intended to modify the solubility characteristics of the polymeric co-ordination compounds formed according to the present invention, but it may also affect their other properties, such as for example, mechanical strength and electrical resistance. Some changes in the chemical composition of the primarily formed polymeric co-ordination compounds corresponding to the general formulae I or II, as specified in the preceeding section, may also occur as result of the baking operation.

The following examples, not to be considered as limitative, illustrate means for preparing the new polymeric co-ordination compounds of this invention and their uses. In the following examples parts are by weight, unless otherwise specified.

EXAMPLE 1

Preparation of Ligand A: 200 parts of benzene were placed in a 1.5 l reaction flask and the system was purged with nitrogen. 13.4 parts of terephthalaldehyde were added to the reaction vessel and the temperature was raised to 50° C. 60 parts of the 1-amino-2-hydroxy-3-N,N,isooctyl-benzyl-amino propane diluted with 30 parts of benzene were added to the reaction mixture. Temperature of 48°–50° was maintained for 2 hours and then an azeotropic distillation was started and continued for 5 hours. Circa 3.5 parts of water were collected. Benzene was removed in a rotavapor from the reaction product which was further stripped from volatile ingredients at 50°–60° C./0.1 torr. 69 parts of the product were obtained. Its molecular weight determined by acidimetric titration was 680 (calculated—683) and the pmr spectrum of the carbon chloride solution of the thus obtained ligand A was characterized by the following peaks: singlets of 8.13 δ; 7.62 δ and 7.20 δ (intensities in the ratio 1:2:5) a broad peak at 4.4 δ (intensity 1) and multiplets or broad peaks at 3.9 δ; 2.5 δ; 2.5 δ; 2.25 δ; 1.2 δ and 0.85 δ.

The following structure could be assigned to ligand A:

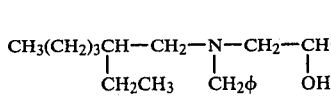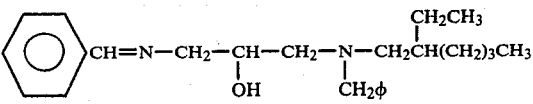

EXAMPLE 2

Preparation of ligand B: Conditions of preparation of ligand B were identical with those described in Example 1, except that 48 parts of the 1-amino-2-hydroxy-N,N-butyl benzyl-amino-propane were added instead of 60 parts of the N,N isooctyl benzyl derivative used in the preparation of Ligand A. 57.3 parts of the product were thus obtained. Its molecular weight determined by acidimetric titration was 570 (calculated—570.8), and the pmr spectrum of the carbon tetrachloride solution of the thus obtained ligand B was characterized by the following peaks: singlets at 8.12 δ; 7.41 δ and 7.20 δ (intensities in the ratio 1:2:5) a braod peak of intensity 1 at 3.2 δ and multiplets or broad peaks at 3.85 δ; 3.50 δ; 2.50 δ; 1.30 δ at 0.85 δ.

The following structure could be assigned to ligand B:

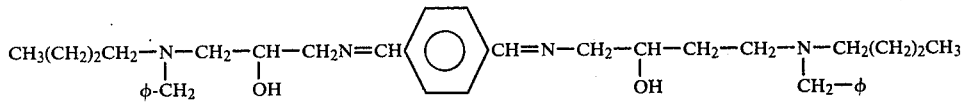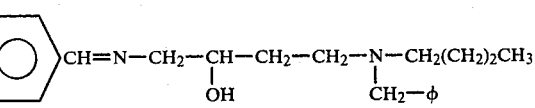

EXAMPLE 3

Preparation of Ligand C: Conditions of preparation of Ligand C were identical with those described in example 1, except that 45 parts of 1-amino-2-hydroxy-3-N,N,-butyl phenyl-amino-propane were added instead of 60 parts of the N,N-isooctyl-benzyl derivative used in the preparation of Ligand A. 54.5 parts of the product were thus obtained. Its molecular weight determined by acidimetric titration was 542.3 (calculated 542.8) and the pmr spectrum of the carbon chloride solution of the thus obtained ligand C was characterized by the following peaks: singlets at 8.12 δ; 7.5 δ; 7.1 δ and 6.7 δ (their intensities in the ratio (1:2:2:3) a broad peak of intensity 1 at 4.1 δ and multiplets or broad peaks at 3.85; 3.55, 2.5, 1.3 and 0.85 δ.

The following structure could be assigned to ligand C:

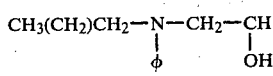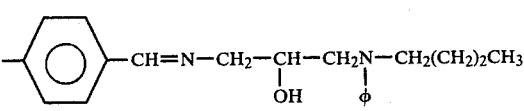

EXAMPLE 4

68 parts of Ligand A were dissolved in 500 parts of toluene and diluted with additional amount of toluene to obtain 1000 parts of the solution. 13.6 parts of solid anhydrous zinc chloride were added to this solution and the mixture was stirred at room temperature for 3–5 hours until the zinc chloride added was dissolved. The thus obtained solution was diluted tenfolds with toluene and poured into a flat container to form 5 mm thick layer. Solvent was evaporated at room temperature at 100 torr, and then at 1 hour/80° C. Glossy dark yellow coating of the surface of the container was thus obtained. It was soluble in acetone and in THF, but insoluble in toluene, carbon tetrachloride and petrol ether. The thus obtained solid coating was baked for 4 hours at 140° C. After this treatment it was resistant to alcohol, $CCl_4$, $CHCl_3$, petrol ether, aromatic hydrocarbons and water, but poorly resistant to acetone, tetrahydrofurane and dimethyl formamide. The elemental analysis of the thus obtained material was as follows: C—65.7%; H—7.5%, N—6.3%, O—3.9%, Cl—8.7%, Zn—7.9%.

EXAMPLE 5

1000 parts of toluene solution of the $ZnCl_2$ complex of Ligand A were prepared in an identical fashion as in example 4, except that 204 parts of Ligand A and 40.9 parts of $ZnCl_2$ were used for its preparation. The thus obtained solution was further concentrated in a rotavapor and then the viscous liquid was poured into an open container and toluene was completely removed in a vacuum oven. Thus obtained solid material was broken into small flakes and kept for 4 hours at 140° C. The elemental analysis of thus obtained product was identical with that described in example 4.

EXAMPLE 6

Flakes of the polymeric co-ordination compound containing $ZnCl_2$, which was prepared as described in example 5, were fed into an injection molding machine and shaped into cylindrical objects by injection molding at 160° C. and 50 atm. The tensile strength of thus produced polymeric materials was found to be 150 $Kg/cm^2$.

EXAMPLE 7

One part of flakes of the polymeric co-ordination compound containing $ZnCl_2$, which was prepared as described in example 5 was mixed with 2 parts of a low density polyethylene and the mixture was fed into an injection molding machine. Objects obtained by injection molding of such mixtures were flexible and homogeneous. Intimate blending of the two polymers was indicated by the results of DSC measurements of the blend. Namely, while the crystallinity of the unblended polyethylene was 24%, it decreased to 14% as result of blending.

EXAMPLE 8

Polymeric coordination compound of Ligand A with iron was prepared as described in example 4 except that 19.9 parts of $FeCl_2 \cdot 4 H_2O$ instead of $ZnCl_2$ were used in its preparation. A dark brown glossy coating was thus obtained. It was highly resistant to alcohol, water, $CCl_4$ and aromatic and aliphatic hydrocarbons and fairly resistant to acetone, chloroform and THF. The elemental analysis of thus obtained product was as follows: C—65.5%, H—8.3%, N—7.2%, O—3.8%, Cl—8.1%, Fe—7.1%.

EXAMPLE 9

Polymeric coordination compound of Ligand A with iron was prepared as described in example 4 except that 22.6 parts of $FeBr_3$ instead of $ZnCl_2$ were added for its preparation and equal parts of toluene and tetrahydrofurane were used as a solvent instead of pure toluene.

The elemental analysis of thus obtained product was as follows: C—54.9%, H—6.9%, N—6.0%, O—3.2%, Br—22.9%, Fe—6.1%.

EXAMPLE 10

Polymeric coordination compound of Ligand A with copper was prepared as described in Example 4 except that 17 parts of $CuCl_2 \cdot 2H_2O$ instead of $ZnCl_2$ were used in its preparation. The dark green glossy coating obtained after the solvent was evaporated at R. T. turned brown after the baking operation. The elemental analysis of thus obtained product was as follows: C—64.4%; H—7.1%; N—7.0%, O—3.5%; Cl—9.5%; Cu—8.5%.

EXAMPLE 11

Polymeric coordination compound of Ligand A with silver was prepared as described in example 4 except that 12 parts of $AgNO_3$ instead of $ZnCl_2$ were used in its preparation. After the solvent was evaporated and sample was heated to 80° for 1 h a mirror-like coating was obtained. During baking at 140° it became resistant to organic solvents and water. The elemental analysis of thus obtained product was as follows: C—63%; H—7.6%; N—9.5%; O—7.6%; Ag—12.9%.

EXAMPLE 12

Polymeric coordination compound of Ligand A with antimony was obtained as described in example 4, except that 22.8 parts of $SbCl_3$ instead of $ZnCl_2$ were used in its preparation. A light yellow brittle product was thus obtained.

Its elemental analysis was as follows: C—56.8%; H—7.3%; N—7.2%; O—4.1%; Cl—11.4%; Sb—13.1%.

EXAMPLE 13

A polymeric coordination compound of Ligand A with titanium was obtained as described in example 4 except that 19.0 parts of $TiCl_4$ were used in its preparation and chloroform instead of toluene was used as a solvent. Dark brown product was thus obtained. Its elemental analysis was as follows: C—57.3%; H—6.6%; N—7.3%; O—5.8%; Cl—17%; Ti—6.2%.

EXAMPLE 14

A lead containing polymeric compound was prepared, as described in Example 4 except that 16.6 parts of $Pb(CH_3COO)_2 3H_2O$ were used in its preparation. The product remained, however, semi-liquid after the solvent was evaporated at room temperature and turned into an elastic dark yellow material after several hours of baking at 140°.

Its elemental analysis was as follows: C—61.6%; H—7.1%; N—7.4%; O—10.1%; Pb—13.8%.

EXAMPLE 15

57 parts of Ligand B were dissolved in 500 parts of chloroform and diluted with additional chloroform to obtain 1000 parts of the solution. 17 parts of $AgNO_3$ crystals were added and further treatment was identical as in example 4, a mirror-like coating was thus obtained. The elemental analysis of thus obtained product was as follows: C—60.1%; H—5.9%; N—10.1%; O—8.9%; Ag—15.0%.

EXAMPLE 16

A silver containing polymeric coordination polymer was prepared, as described in example 15, except that 54.3 parts of Ligand C were used instead of Ligand B. The elemental analysis of thus obtained compound was as follows: C—58.9%; H—5.8%; N—10.5%; O—9.2%; Ag—15.6%.

EXAMPLE 17

Ligand B was synthesized as described in Example 13. 15 mg of ligand B was dissolved in 5 ml of ethylalcohol. The solution was mixed with a solution of 60 mg of $ZnCl_2$ in water and diluted with water to 1000 ml. Aliquot portions of the stock solution were further diluted with water and their anti-cancer activities were checked in vitro by incubating with YAC cells for 2 and 4 hours, respectively. After a [$^3$H] azidine pulse was given, it was again incubated for 1 hour. The reaction was terminated by trichloroacetic acid precipitation. It was found that the percent inhibition of the [$^3$H] azidine incorporation is 39% and 83% after 2 and 4 hours of incubation, respectively, when the concentration of Ligand B is 15 μg/ml. Per cent inhibition decreases to 40% after 4 hours when 7.5 μg/ml of Ligand B are used.

I claim:

1. Polymeric compounds of formulas (I) and (II)

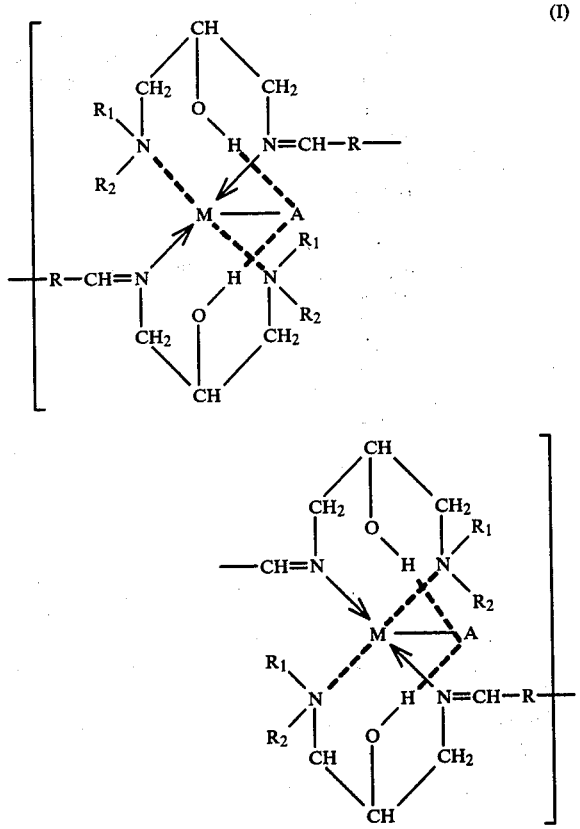

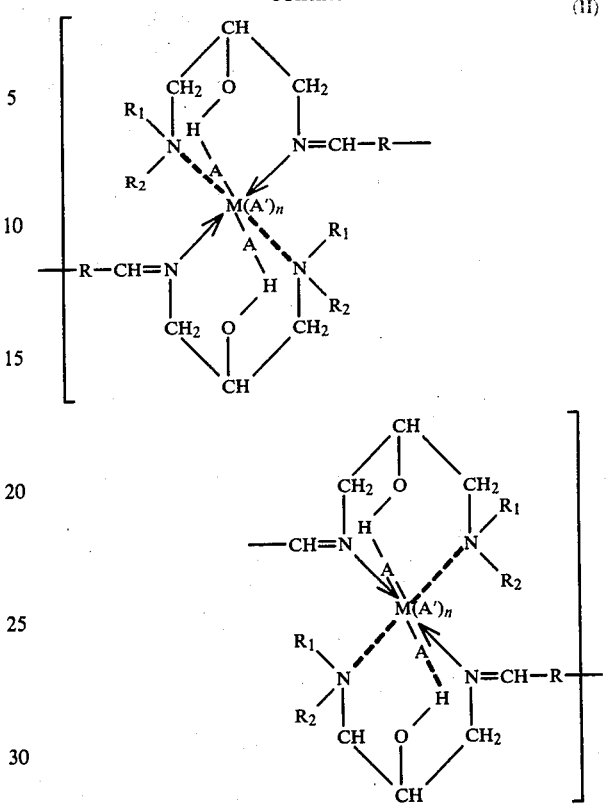

wherein
R designates a bivalent aromatic hydrocarbon group,
$R_1$ and $R_2$ designate monovalent hydrocarbon groups,
M is a metal cation capable of forming coordination bonds with imino- and amino-nitrogen atoms,
A and $A^1$ are anions acting as counter ions of M,
n is zero or an integer depending on the valency of M.

2. A polymeric compound according to claim 1 where M is selected from Ag, Zn, Cu, Co, Ni, Mn, Fe, Ti, Pt, Sb and Pb ions.

3. A polymeric compound according to claim 1, wherein the polymer is the reaction product of an aromatic dialdehyde with an β-hydroxy-α,γ-diamine which is subsequently reacted with an inorganic salt.

4. A polymeric compound according to claim 1, being the reaction product of terephthalaldehyde and 1-amino-2-hydroxy-3,N,N-butyl-benzylaminopropane and the subsequent reaction of the thus obtained intermediate with a suitable salt.

5. A process for the production of polymers of Formula I and II defined in claim 1 which comprises:
a. Condensing an aromatic dialdehyde with a β-hydroxy-α,γ-diamine to form the "monomeric" polydentate ligand;
b. preparing a solution of the "monomeric" polydentate ligand in an organic solvent, preferably an aprotic volatile solvent, such as toluene or chloroform;
c. dissolving a chosen inorganic salt in the "monomeric" polydentate ligand solution;
d. evaporating of the solvent from the thus obtained solution to result in a solid product in the form of a thin layer, powder or flakes.

6. A process according to claim 5 wherein the product is baked at a temperature of from 100° to 150° C. to modify its solubility and physical properties.

7. A process according to claim 5 wherein the inorganic salt is selected from silver nitrate, zinc chloride, copper chloride, copper nitrate, cobalt chloride, nickel chloride, manganese chloride, platinum chloride, iron chloride, iron bromide, titanium chloride, antimony chloride, lead acetate and similar salts.

* * * * *